US007923248B2

(12) United States Patent  
Ferrie et al.

(10) Patent No.: US 7,923,248 B2
(45) Date of Patent: Apr. 12, 2011

(54) METHODS FOR PRODUCING MICROSPORE DERIVED DOUBLED HAPLOID *APIACEAE*

(75) Inventors: Alison M. R. Ferrie, Saskatoon (CA); Marie L. Mykytyshyn, Saskatoon (CA); Terry Bethune, Saskatoon (CA)

(73) Assignee: NRC, Ottawa, ON ( * ) Notice: Subject to any disclaimer, the term of this patent is extended or adjusted under 35 U.S.C. 154(b) by 326 days.

(21) Appl. No.: 11/920,846

(22) PCT Filed: May 24, 2006

(86) PCT No.: PCT/CA2006/000846
§ 371 (c)(1),
(2), (4) Date: Sep. 18, 2008

(87) PCT Pub. No.: WO2006/125310
PCT Pub. Date: Nov. 30, 2006

(65) Prior Publication Data
US 2009/0100538 A1 Apr. 16, 2009

Related U.S. Application Data

(60) Provisional application No. 60/684,126, filed on May 24, 2005, provisional application No. 60/772,805, filed on Feb. 13, 2006.

(51) Int. Cl.
C12N 5/00 (2006.01)
C12N 5/02 (2006.01)
(52) U.S. Cl. ........................... 435/420; 435/410
(58) Field of Classification Search .................. 435/410, 435/420
See application file for complete search history.

(56) References Cited

U.S. PATENT DOCUMENTS

| | | | |
|---|---|---|---|
| 4,840,906 A | 6/1989 | Hunter |
| 5,322,789 A | 6/1994 | Genovesi et al. |
| 5,445,961 A | 8/1995 | Genovesi et al. |
| 5,492,827 A | 2/1996 | Dirks |
| 5,639,951 A | 6/1997 | Bosemark et al. |
| 5,900,375 A | 5/1999 | Simmonds et al. |
| 6,200,808 B1 | 3/2001 | Simmonds et al. |
| 6,362,393 B1 | 3/2002 | Konzak et al. |
| 6,764,854 B2 | 7/2004 | Konzak et al. |
| 6,812,028 B1 | 11/2004 | Kasha et al. |
| 2002/0151057 A1 | 10/2002 | Zheng et al. |

OTHER PUBLICATIONS

Shariatpanahi et al. Stresses applied for the re-programming of plant microspores towards in vitro embryogenesis Physiologia Plantarum (2006) 127(4) 519-534. Apr. 2006.*
Office Action dated Nov. 11, 2009 on corresponding European application 06 741 557.0.
Office Action of May 20, 2010 on corresponding European application 06 741 557.0.

International Search Report and Written Opinion on International Application PCT/CA2006/000846, Sep. 19, 2006, Alison M.R. Ferrie et al.
Matsubara et al. Acta Horticulturae. 392:129-137 (1995).
Tyukavin et al. Russian Journal of Plant Physiology. 46(6):876-883 (1999).
Andersen et al. In: Biotechnology in Agriculture and Forestry, Bjaja ed. (Berlin: Springer-Verlag) vol. 12, pp. 393-402 (1990).
Hays et al. In: Doubled Haploid Production in Crop Plants, Maluszynski ed. (Dordrecht: Kluwer Academic Publishers) Ch. 2.1, pp. 5-14 (2003).
Lionneton et al. Plant Cell Reports. 20:126-130 (2001).
Ferrie et al. Acta Physiologiae Plantarum. 27(4B):735-741 (2005).
Gorecka et al. J. Appl. Genet. 46(3):265-269 (2005).
Ferrie et al. In: In vitro Embryogenesis in Plants, Thorpe ed. (Dordrecht: Kluwer Academic Publishers) Ch. 9, pp. 309-344 (1995).
Ferrie et al. In: Biotechnology in Agriculture and Forestry, Pua & Douglas eds. (Berlin: Springer-Verlag) vol. 54, pp. 149-168 (2004).
Arnison et al. Plant Cell, Tissue and Organ Culture. 20:217-222 (1990).
Barro et al. Plant Breeding. 118:79-81 (1999).
Brossa. Critical Reviews in Biochemistry and Molecular Biology. 34:339-358 (1999).
Chu. Science Press. 43-50 (1978).
Cordwener et al. Planta. 195:50-56 (1994).
Dunwell. In: Plant Tissue Culture and its Agricultural Applications, Withers and Alderson eds. (Butterworth: London) (1986).
Fabijanski et al. Plant Cell, Tissue and Organ Culture. 26:203-212 (1991).
Fan et al. Protoplasma. 147:191-199 (1988).
Ferrie et al. In Vitro Cellular and Developmental Biology—Plant (2005). accepted—need full citation.
Ferrie et al. In: Biotechnological Applications of Plant Cultures, Shargool and Ngo eds. (CRC Press: Boca Raton) pp. 77-110 (1994).
Ferrie et al. Plant Cell Reports. 14:580-584 (1995).
Ferrie et al. In: Plant Cell, Tissue and Organ Culture: Fundamental Methods, Gamborg and Phillips eds. (Berlin: Springer-Verlag) pp. 155-164 (1995).
Ferrie et al. Plant Cell, Tissue and Organ Culture. 57:79-84 (1999).
Gaillard et al. Plant Cell Reports. 10:55-58 (1991).
Gamborg et al. Exp. Cell Res. 50:151-158 (1968).
Grove et al. Nature. 281:216-217 (1979). Kao et al. Planta. 126:105-110 (1975).
Keller et al. Z. Pflanzenzuchtg. 80:100-108 (1978).
Kott et al. Can. J. Bot. 66:1658-1664 (1988).
Krishna. J. Plant Growth Reg. 22:289-297 (2003).
Lichter. Z. Pflanzenphysiol. 105:427-434 (1982).
Lu et al. Plant Cell, Tissue and Organ Culture. 73:87-89 (2003).
Maheshwari et al. Amer. J. Bot. 69:865-879 (1982).
Nakajima et al. Japanese Journal of Crop Science. 65:114-118 (1996).

(Continued)

*Primary Examiner* — Wendy Haas
(74) *Attorney, Agent, or Firm* — Catherine Eckenswiller

(57) ABSTRACT

The present invention relates to culturing isolated microspores and the subsequent generation of doubled-haploid plant lines that are suitable for the rapid selection of plants with improved composition and agronomic performance. Processes developed for the recovery of microspore-derived embryos from fennel and caraway may be adapted to related species in the Apiaceae family including, but not limited to, fennel, carrot, dill, anise, lovage, parsnip, and laceflower.

16 Claims, 7 Drawing Sheets

OTHER PUBLICATIONS

Oh et al. Plant Cell Reports. 17:921-924 (1998).
Polsoni et al. Can. J. Bot. 66:1681-1685 (1988).
Pullman et al. Plant Cell Reports. 22:96-104 (2003).
Nitsch et al. Science. 163:85-87 (1969).
Saskaki. Plant Cell, Tissue and Organ Culture. 71:111-116 (2002).
Sasse. In: Brassinosteroids: Steroidal Plant Hormones, Sakurai et al. eds. (Tokyo: Springer-Verlag) 137-161 (1999).
Wilen et al. Physiologia Plantarum. 95:195-202 (1995).
Zhao et al. Plant Cell Reports. 15:668-671 (1996).
Extended Search Report for European Application 06 74 1557.0, published Jan. 23, 2009.
Maluszynski et al. eds. Double Haploid Production in Crop Plants. (Dordrecht: Kluwer Academic Publishers) Ch. 2.3, pp. 205-215 (2003).
Chen et al. Plant Breeding. 113(3):217-221 (1994).

* cited by examiner

| Carbohydrate | Conc. (%) | 32 °C – 3 days (# embryos) | 35 °C – 3 days (# embryos) |
|---|---|---|---|
| Glucose | 25 continuous | 0 | 0 |
| | 25 to 17 | 9 | 104 |
| | 25 to 15 | 0 | 9 |
| | 25 to 13 | 19 | 69 |
| | 25 to 10 | 0 | 0 |
| Fructose | 25 continuous | 0 | 0 |
| | 25 to 17 | 0 | 1 |
| | 25 to 15 | 0 | 0 |
| | 25 to 13 | 0 | 0 |
| | 25 to 10 | 0 | 4 |
| Raffinose | 16 continuous | 0 | 0 |
| | 16 to 8 | 0 | 0 |
| Melibiose | 25 continuous | 0 | 0 |
| | 25 to 17 | 0 | 0 |
| | 25 to 15 | 0 | 0 |
| | 25 to 13 | 8 | 3 |
| | 25 to 10 | 2 | 9 |
| Maltose | 25 continuous | 0 | 0 |
| | 25 to 17 | 7 | 0 |
| | 25 to 15 | 0 | 0 |
| | 25 to 13 | 0 | 0 |
| | 25 to 10 | 0 | 0 |
| Melezitose | 25 continuous | 11 | 0 |
| | 25 to 17 | 0 | 3 |
| | 25 to 15 | 3 | 0 |
| | 25 to 13 | 0 | 0 |
| | 25 to 10 | 0 | 0 |
| Sucrose | 25 continuous | 19 | 0 |
| | 25 to 17 | 18 | 0 |
| | 25 to 15 | 0 | 0 |
| | 25 to 13 | 67 | 0 |
| | 25 to 10 | 9 | 0 |

FIG. 7

| Species | Cultivar/Genotype | Medium/culture conditions | Embryos transferred |
|---|---|---|---|
| Anise | Breeding line 1 | NLN-25, 32-3 or 24C | 365 |
| Carrot | Nantes Touchon | NLN-25 + 10uM ACC, 32-7 | 114 |
| Dill | Mammoth<br>Hercules<br>Fernleaf | NLN-25, 32-7 or 14<br>NLN-17, 32-7<br>NLN-13, 32-3 | 10<br>10<br>35 |
| Parsnip | Hollow Crown | NLN-25, 32-7 | 150 |
| Lovage | 1 | NLN-25, 32-3 | 35 |
| Leaf fennel | 1 | NLN-25 + GA, 35-3 15/10 donor plants | 310 |

FIG. 8

# METHODS FOR PRODUCING MICROSPORE DERIVED DOUBLED HAPLOID *APIACEAE*

CROSS-REFERENCE TO RELATED APPLICATIONS

The present application is a national entry of International Patent Application No. PCT/CA2006/000846, filed on May 24, 2006, and claims the benefit under 35 U.S.C. §119(e) of U.S. Provisional Patent Application Ser. No. 60/684,126, filed May 24, 2005, and U.S. Provisional Patent Application Ser. No. 60/772,805, filed Feb. 13, 2006, the contents of all of which are incorporated herein in their entirety by this reference.

TECHNICAL FIELD

The invention relates generally to biotechnology, more particularly, the present invention relates to methods for generating doubled haploid plants from microspores and the compositions of plant matter obtained therefrom.

BACKGROUND

Fennel is a hardy, erect, umbelliferous herb of the family Apiaceae (Umbelliferae). Fennel has been used since ancient times as a flavouring agent in food. Essential oils and oleoresins derived from fennel are used in soaps, perfumes, creams, and liqueurs. Additionally, fennel has medicinal properties including uses as an antispasmotic, carminative, diuretic, expectorant, and laxative.

Fennel is an annual or perennial herb which can reach a height of 1.5 meters and has yellow flowers on a compound umbel. Two varieties of fennel are recognized that are thought to originate from subspecies *capillaceum*: Sweet or Roman fennel, subspecies *capillaceum* (Galib) Holmboe var. *dulce* Mill, and bitter or wild fennel, subspecies *capillaceum* (Galib) Holmboe var. *vulgare* Mill. Approximately 60% of the essential oil in the fennel plant is localized in the fruit, (commonly fennel seed) with the remaining portion lying within the other green parts of the plant. The oils of sweet and bitter fennel differ in their constitutive components. Bitter fennel oils are higher in fenchone or limonene and sweet fennel oils have a greater amount of anethone. The properties of sweet fennel oil are considered to be of higher quality due to a more pleasant aroma and flavour.

*Foeniculum vulgare* ssp. *capillaceum* is grouped into three varieties: *Azoricum*, also known as bulb fennel, Italian fennel, or Florence fennel, an annual that produces a bulb and is grown in Mediterranean countries where it is used as a vegetable. *Dulce*, also know as sweet fennel or French fennel, is mainly used as a condiment and *Vulgare* (bitter fennel), a perennial, has an essential oil content higher than that of dulce.

Fennel seed is used in the food industry as a flavouring agent for meats, vegetables, fish, soups, salad dressings, stews, breads, pastries, teas, and alcoholic beverages. The essential oils derived from fennel are used in condiments, soaps, creams, and perfume. The medicinal or nutraceutical applications of fennel include uses as an: antispasmodic, carminative, diuretic, expectorant, laxative, and stomachic. Additionally, fennel is used as a lactation stimulant, a remedy for colic, and as a treatment of gastroenteritis, hernia, indigestion, abdominal pain, and dissipation of phlegm.

Another species of the Apiaceae family is Caraway, *Carum carvi* L., a biennial herb which is native to Europe and Western Asia, but also grown on the prairie provinces of Canada. First year caraway plants resemble carrots, growing to about 8 inches tall with finely divided leaves and long taproots. By the second year, two to three foot stalks develop topped by umbels of white or pink flowers. The seeds are typically relatively small, brown and crescent shaped.

The Caraway seed is used whole as a spice or crushed to produce caraway oil. The seeds have a licorice flavour and are used in breads, soups, spreads, salad dressings, liqueurs, and the like. The leaves can be used in cooking, as can the roots. Caraway seeds and oil have medicinal applications for disorders such as rheumatism, eye infections, toothaches, and nausea. Caraway oil has some anti-bacterial properties.

The main constituent of caraway seed oil is carvone and limonene. Carvone has been used as a spice in foods, a sprouting inhibitor for potatoes and as a growth inhibitor for fungi and insects. The oil can also be used a fragrance component in cosmetics (e.g., soaps, creams, lotions, and perfumes).

Other species of the Apiaceae family include root crops (e.g., carrot, parsnip); stem, leaf, and petiole crops (e.g., celery, parsley); and seed crops (e.g., dill, anise, caraway). These species are used for foods, flavouring of foods, perfumes, medicines, and animal feed. Carrot is a major food crop, but can also be used as a food colouring agent in butter and as a sweetener of liqueurs. Anise is a licorice flavoured herb and is used to flavour liqueurs, candies, and toothpaste.

The use of doubled-haploid plants as a vehicle for plant breeding is well established and has become a routine practice for breeders of crops such as canola, wheat, barley, and maize. The main advantage of generating doubled-haploid plants from a cell culture is the greatly reduced time required to achieve homozygosity; years of selfing and recurrent selection are replaced by a single culture cycle. The use of haploid technologies results in the fixation of traits, allowing for efficient screening and selection of desirable phenotypes.

Haploid plants that comprise only a single set of chromosomes are infertile and must be doubled in their chromosome complement before use in breeding. Techniques for doubling the chromosome number in haploid plants using colchicine and other chemicals that disturb the cytoskeleton of cells are well known in the literature (e.g., Zhao et al., 1996).

There are several methods for generating doubled haploid plants. Haploid plants naturally occur with low frequency and can be identified in field grown populations based on examination of flower morphology. The low frequency of occurrence makes this approach impractical (See. e.g., U.S. Pat. No. 5,639,951). Haploid plants may also result from wide hybridization followed by chromosome elimination.

Wide hybridization was used to create *Hordeum bulbosum* by crossing common barley, *Hordeum vulgare* with *H. bulbosum* and the subsequent elimination of *H. bulbosum* chromosomes. Wide hybridization has been used to develop barley, wheat, maize, sorghum, and millet cultivars but has limited use outside of these cereal crops.

Another method for generating doubled haploid plants is gynogenesis. Gynogenesis involves the culture of female cells such as unfertilized ovaries or ovules. This method has only been shown to work with a few species and the frequency of embryo formation is low (See, e.g., U.S. Pat. No. 5,492,827).

Doubled-haploid plants can also be generated by androgenesis. Androgenesis involves culturing developing microspores with the entire anther or physically disrupting the anther and culturing the isolated microspores.

The development of embryos, haploid, and doubled-haploid plants from developing microspore in culture has been achieved to date in a variety of species representing many different genera (Dunwell, 1986; Ferrie et al., 1994). It is well known that a large variety of factors influence the success of inducing embryo development from isolated microspores or from anther cultures. (Ferrie and Keller, 1995; Maheshwari, et al., 1982).

One critical aspect of the methods for inducing embryo formation from microspores is to disrupt and shift the microspore developmental process using physical or chemical means. The disruption and shift must coincide with the developmental stage of the microspore that subsequently allows embryo formation. Typically the stage that is disrupted is the late uninucleate to early bi-nucleate stage of development (Gaillard et al., 1991; Kott et al., 1988; Fan et al., 1988). Historically, the chief agent for disruption was elevated temperatures, (Keller et al., 1978; Cordewener et al., 1994) but chemicals such as colchicine, cytochalasin B, and trifluralin that are known to disturb cellular cytoskeleton organization have more recently been shown to be effective as well (See e.g., U.S. Pat. Nos. 5,900,375; 6,200,808).

The nutrient medium is another aspect that has been shown to be important for recovery of embryos from induced microspores. Both the mineral composition of the medium and the percent of carbohydrates have been shown to be critical factors for some applications. High concentrations of sucrose (e.g., 13%) or other specific sugars such as maltose have been shown to be important. However, the optimal composition of the medium for embryo induction differs greatly from species to species. In addition to sugars and salts, plant growth regulators such as auxins, cytokinins and/or gibberellins may be required. Various gametocidal chemicals such as 2-hydroxynicotinic acid, 2-chloroethyl-phosphonic acid, and pronamide as well as undefined natural factors emanating from ovules (See e.g., U.S. Pat. Nos. 6,764,854; 6,362,393) may also be required components of the optimal nutrient medium.

There are vast differences between optimal nutrient media for the induction of embryos. In U.S. Pat. No. 4,840,906, spikes containing anthers were pretreated at 4° C. for a period of up to 28 days prior to culture of the barley microspores on media with varying sugar composition. This revealed the stimulative effect of maltose on the barley microspores. In U.S. Pat. Nos. 5,322,789 and 5,445,961, where isolated microspore and anther cultures of corn involved pre-treatment of microspores at 10° C., the requirement for mannitol and the chromosome doubling agent colchicine in the culture medium was demonstrated. These and other methods developed for cereal crops have the limitation that the methods may result in formation of significant numbers of albino plants.

U.S. Pat. No. 6,362,393 discloses a method for the production of doubled-haploid plants from wheat involved subjecting developing microspores to temperature and nutrient stress. A medium comprised of mannitol, maltose, auxins, cytokinins and/or gibberellin plant growth regulators, as well as a specific sporophytic development inducing chemical, were required for optimal embryo development. U.S. Pat. No. 6,764,854 describes an application of the above method for the production of doubled-haploid rice. U.S. Pat. No. 6,812,028 demonstrates a method for regeneration of isolated barley microspores that includes low temperature pretreatment, arabinogalactan protein, auxins and unknown natural factors from ovaries.

Brassinosteroids (BRs) are a group of plant growth-promoting substances that are similar to animal steroid hormones. They were first isolated from *Brassica napus* pollen in 1979 (Grove et al., 1979), but are known to be present in many plant species ranging from algae to higher plants. BRs are active at very low concentrations and can influence many plant growth and developmental processes, including cell elongation, cell division, and cell differentiation (Brosa, 1999). In addition to their role in plant growth and development, BRs have also been shown to protect plants from both abiotic and biotic stresses (Krishna, 2003). There are over 60 different BRs identified, with brassinolide (BL) and 24-epi-brassinolide (EBR) being the most active of the known compounds for exogenous applications. These compounds have been used in plant tissue culture applications, leading to increases in the freezing and thermotolerance of cell suspensions (Wilen et al., 1995), induction of somatic embryogenesis in conifers and rice (Pullman et al., 2003), stimulation of shoot regeneration in *B. oleracea* var. *botrytis* and *Spartina patens* (Sasaki 2002; Lu et al., 2003), promotion of cell division in Chinese cabbage protoplasts (Nakajima et al., 1996), and increase in the rate of cell division in leaf protoplasts of *Petunia hybrida* (Oh et al. 1998). BRs have been tested in microspore embryogenesis of *Brassica* species and results showed an increase in embryogenesis (Ferric et al., 2005).

Isolated microspore culture protocols have been described for various *Brassica* species, (Ferrie et al., 1995, 1999, 2004; Barro et al. 1999; and Lionneton 2001). Factors that have been identified that contribute to induction and development of microspore-derived embryos included growth conditions of the parent plants, stage of microspore development, temperature stress, osmotic stress, and carbohydrate composition of the medium. The requirement for temperature stress may be replaced by chemical inhibitors of cytoskeleton integrity (See, e.g., U.S. Pat. Nos. 5,900,375 and 6,200,808).

Despite the successful development of embryos from microspores of numerous species, many species remain unresponsive. *Arabidopsis thaliana* is an example of a recalcitrant species that does not respond to methods that are known to succeed for the closely related *Brassica* species. Additionally, it is well known by those of ordinary skill in the art that response to microspore culture varies from cultivar to cultivar and from plant to plant of the same cultivar, suggesting unknown genetic influences.

SUMMARY OF THE INVENTION

An embodiment of the present invention discloses a process for culturing isolated microspores (immature pollen) and the subsequent generation of doubled-haploid plant lines that are suitable for the rapid selection of fennel with altered/improved composition and agronomic performance.

Another embodiment of the present invention discloses a process for culturing isolated microspores (immature pollen) and the subsequent generation of doubled-haploid plant lines that are suitable for the rapid selection of caraway with altered and/or improved composition and agronomic performance.

In other embodiments, the processes for the recovery of microspore derived embryos from fennel and caraway may be adapted to related species in the Apiaceae family including, but not limited to, carrot, dill, anise, lovage, parsnip, angelica, and laceflower.

Another embodiment of the invention is a process for producing doubled-haploid plants of fennel and/or caraway, comprising: cultivating microspore donor plants under conditions that allow the development of microspores capable of development into haploid embryos; isolating microspores at a stage of development (uninucleate to early binucleate) that can be induced to develop embryos in culture; culturing isolated microspores in media with effective amounts of mineral and carbohydrate under culture conditions that induce embryo development in microspores; and generating doubled-haploid plants.

In a further embodiment, the invention discloses processes for developing microspore doubled-haploid plants from species related to fennel and caraway in the family Apiaceae including, but not limited to, carrot (*Daucus carota*), angelica (*Angelica archangelica* L.), anise (*Pimpinella anisum* L.) dill (*Anethum graveolens* L.), laceflower (*Amni majus*), lovage (*Levisticum officinale* Koch.), and parsnip (*Pastinaca sativa* L.).

In a further embodiment, the invention discloses a microspore-derived doubled haploid plant or plant cell and microspore-derived embryos produced by methods of the present invention. As used herein, the term "plant" refers to plants and plant cells.

Advantageously, the plant lines may also include novel composition of essential oils and/or oleoresin.

BRIEF DESCRIPTION OF THE DRAWINGS

FIG. 7. Effect of medium carbohydrate composition and movement from high to lower sugar concentration on microspore embryogenesis of vegetable fennel VF-10.

FIG. 8. Process for inducing embryos from culture of isolated microspores of various Apiaceae species.

BEST MODE OF THE INVENTION

Figure 1:
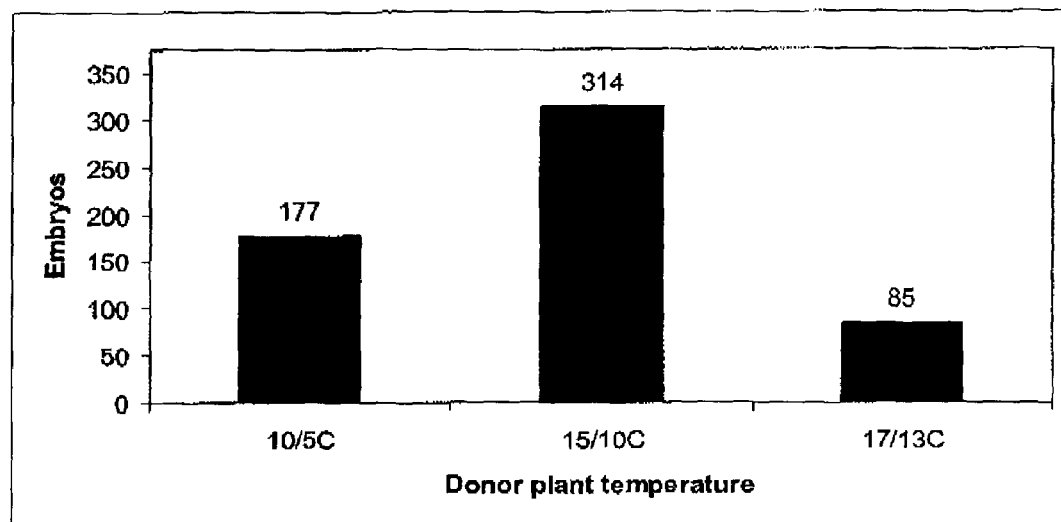
FIG. 1. Effect of donor plant conditions on microspore embryogenesis of vegetable fennel.

Microspore Culture of Fennel.

Isolated microspore culture is a plant breeding tool that can be used to rapidly produce uniform homozygous lines that may be evaluated for improved agronomic performance and the production of novel compositions.

Successful methods of anther and isolated microspore culture have been reported for a variety of species identifying a large number of different factors critical to successful embryo induction. In order to efficiently develop an effective process for fennel, the following strategy was employed.

Although anther and microspore culture has been successful with many species, results are often only achieved with certain cultivars or genotypes indicating that undefined genetic parameters influence the success of the culture process.

The vegetable fennel lines (VF1, VF2, VF3, VF4, VF5, VF6, VF7, VF8, VF9, VF10) were obtained from Rijk Zwaan (Rijk Zwaan Zaadteelt en Zaadhandel B.V., P.O. Box 40, 2678 ZG de Lier, Holland). The oilseed fennel line LF1 was from obtained from Richters (Richters, Goodwood, Ontario, L0C 1A0).

In consideration of the known variability in capacity of materials of differing genetic origin, testing of a variety of different lines is an important strategy. Different genotypes may be subjected to studies in series (one after the other), all together, or in representative groups. The larger the range of materials tested, the greater the chance that responsive material will be identified quickly.

Regardless of the individual species or genotype selected, it is well established that successful microspore culture methods require microspores to be at a developmental stage where they are competent to respond to embryo induction. This stage is typically the mid- to late-uninucleate to early binucleate stage of development just prior to the first microspore mitosis. The importance of the mitotic process is further confirmed by induction of embryo formation in some circumstances by chemicals, such as colchicine, that are known to inhibit microtubule formation of the spindle apparatus.

In some plant species, the size of the flower bud may be used as a marker of microspore development as the majority of microspores develop at similar rates within the anther. For instance, in the well-studied species *B. napus*, the bud size typically correlated with the uninucleate stage of microspore development is 3-4 mm. The more diminutive flowers of fennel were shown to comprise mainly of uninucleate microspores when buds were 1-3 mm in length. Buds that were green and tightly closed were selected.

It is expected that the conditions for the growth of donor plants and pre-conditioning of plant tissues comprising the developing microspores may have an impact on both the rate of maturation of microspores and the physiological competence of these cells to respond to culture. In cereal crops, it has been widely shown that pre-culture of spikes containing the anthers at low temperatures (4-10° C.) for prolonged periods of up to 28 days is needed for optimal response. Generally, in dicotyledonous species, pre-culture is either ineffective or inhibitory. Dicotyledonous species such as *Brassica* may be favourably influenced by temperate or cool growth conditions of donor plants. *Saponaria* plants were shown to respond best when grown at temperature regimes of 20/15° C. with a 16 hour photoperiod. Plants grown at lower temperatures were shown to be much less responsive. Pre-treatment of harvested buds at low temperature prior to culture has only been shown to be effective for cereal crops.

The number of temperature treatments that could be tried to precondition donor plants is very large. Therefore, fennel plants were initially grown under a day/night temperature regime of 20/15° C. with a 16 h photoperiod. Six weeks prior to harvest of microspores for culture, some donor plants were moved to growth chambers with 10/5° C., 15/10° C., or 17/13° C. day/night temperature regimes. The best donor plant conditions for embryo production were 15/10° C. day/night temperature regime (FIG. 1).

Figure 2:
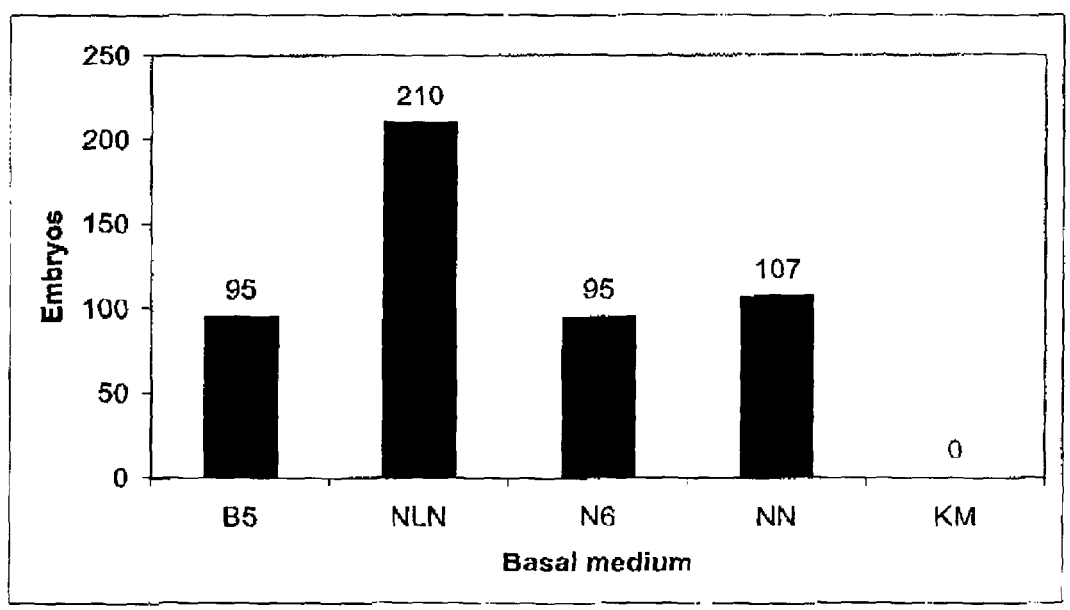
FIG. 2. Effect of basal medium on microspore embryogenesis of vegetable fennel.

The composition of the basal medium is another factor that has been shown to influence the response of isolated microspores to culture. In order to optimize the culture medium for fennel, a number of different basal medium compositions were evaluated that included: B5 (Gamnborg, 1968), NLN (Lichter, 1982), N6 (Chu, 1978), NN (Nitsch, et al., 1969), and KM (Kao, et al., 1975). Embryos were produced on four of the five basal media tested (FIG. 2) with NLN being the most effective.

One of the key elements of medium composition that has been shown to influence microspore-derived embryo formation is the type and concentration of carbohydrates in the medium. Cereal crops, in particular, have been shown to benefit from the inclusion of sugar alcohols, such as mannitol, or disaccharides, such as maltose, whereas dicotyledonous species typically respond best to sucrose or glucose. The concentration and resulting percent of carbohydrates in the medium has also been shown to have pronounced effects on the response of cultured isolated microspores. Experiments using different sugars (glucose, fructose, melibiose, maltose, melezitose, and raffinose) at osmolarities similar to 10, 13, 15, 17, and 25% sucrose have been conducted. Some embryos were recovered from media comprising each of the sugars tested. Further experiments evaluated a medium change to a medium with a lower osmolarity and lower carbohydrate concentration. Overall, the greatest number of embryos for all genotypes tested was recovered after elevated temperature induction (35° C.) in NLN medium using glucose as the carbohydrate source. However, at the embryo inductive temperature of 32° C., the best results were achieved with media comprising 25% sucrose (FIG. 7)

A second key element that has been established as pivotal in the induction of embryos from isolated microspores in other species has been the duration and degree of the high temperature treatment needed to re-direct microspore development and induce the formation of embryos. It has been demonstrated that cultured microspores subjected to elevated temperatures undergo a typical heat shock response (Fabijanski et al., 1991) upon exposure to elevated temperatures. Protein synthesis activities decline to low levels and the mitotic division of the nucleus is arrested. The duration and degree of temperature treatment required for optimal embryo formation varies with individual species and may also vary with individual cultivars. The optimal response is not predictable and must be determined experimentally. Generally, cereal crops benefit from incubations in the lower range of 25-28° C. and non-cereal crops benefit from incubations in a higher range of 30-35° C. The duration of elevated temperature incubation needed for optimal response before a return to more ambient temperatures may vary from 1 to 7 days.

Experiments in which fennel microspores were subjected to various, or one continuous, high temperature treatment for 1-7 days demonstrated that embryos were recovered with high temperature induction of 30-35° C.

Another factor that may influence the ability of microspores to respond to culture is the density of cells per volume of medium. It has been demonstrated that the optimal density for *B. napus* microspores is in the range of 40,000-100,000 microspores per mL of culture medium (Fan, et al., 1988; Kott, et al., 1988; Polsoni, et al., 1988). Studies were conducted with fennel microspores at 50,000 and 100,000 cells per mL of culture medium. However, no clear differences in embryo induction were detected. All further experiments used a density of 50,000 microspores per mL.

In addition to sugars and standard inorganic nutrients used for the growth of cells in culture, biochemicals and reagents with known physiological function may also be added to isolated microspore culture media to encourage embryo formation and development or counteract and/or sequester inhibitors of embryo growth and development. Examples of substances that have been found beneficial for embryo formation include auxins, cytokinins, gibberellic acid, $AgNO_3$ (or other ethylene antagonists), activated charcoal, and gametocidal chemicals. Additionally, the response of microspores may be enhanced by unknown naturally produced substances from feeder cells or ovules. For example, isolated microspores of fennel were exposed to media enhanced with physiological concentrations of GA3, colchicine, polyethylene glycol, and/or brassinosteroids.

Isolated Microspore Culture of Caraway

The caraway lines used were designated Moran, NN-1, and NN-2 breeding lines and were obtained from the Dept of Plant Sciences, University of Saskatchewan, Canada. Caraway seeds were planted in 6-inch pots filled with REDI-EARTH™ soil-less mix containing approximately 1 g of slow release fertilizer (14-14-14-Nutricote). The mixture was thoroughly soaked with water and two to five seeds were placed in each pot. Pots were placed in a lighted growth cabinet (20/15° C., 16 h photoperiod, 400 µmol $m^{-2}s^{-1}$) and watered three times per week with 0.35 g/L of 15-15-18 (N-P-K) fertilizer.

Figure 9:
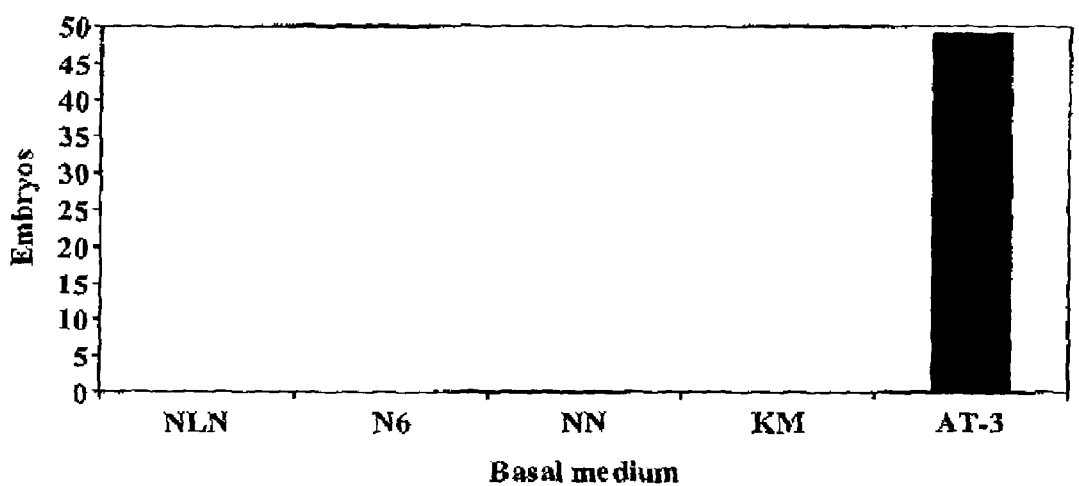
FIG. 9. Embryo production of caraway embryos on B5, NLN, N6, NN, KM, and AT-3 media.
Figure 10:
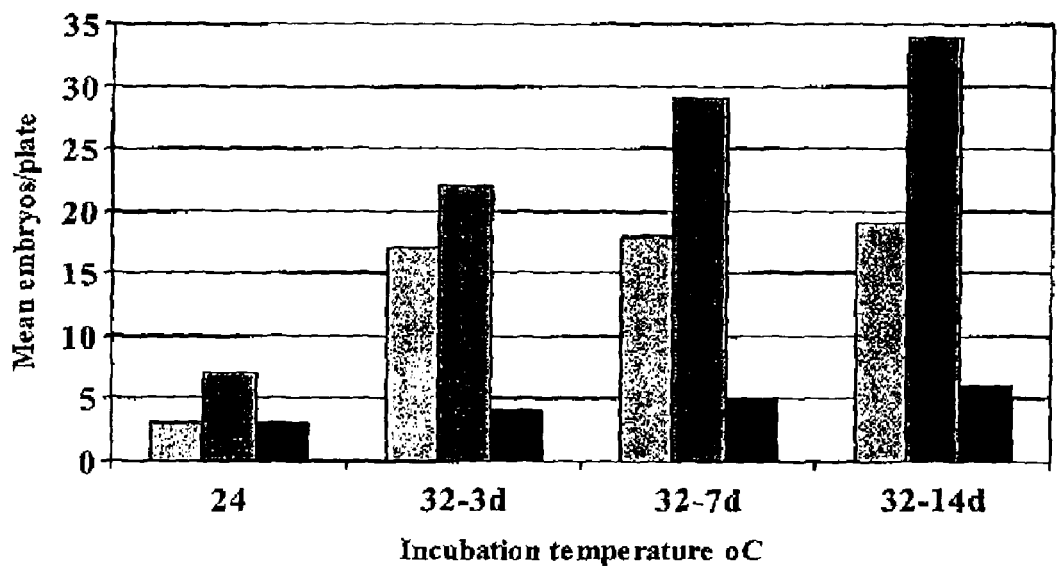
FIG. 10. Effect of incubation temperature and temperature treatment period on microspore embryogenesis of Caraway (var. Moran) grown on AT-3 media. Each bar graph group represents data. The data representing a first harvest, followed seven days later by a second harvest, followed seven days later by a third harvest.
Figure 11:
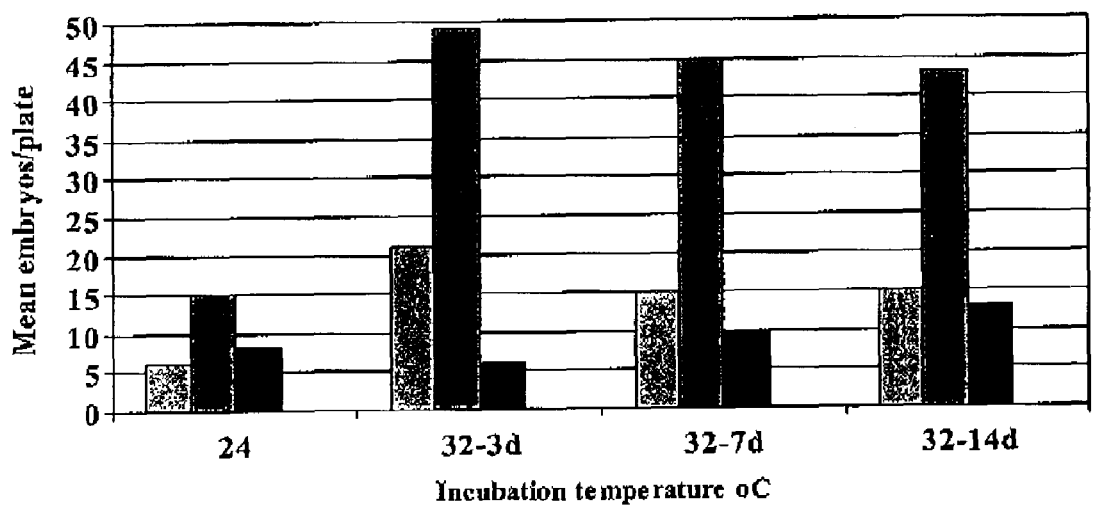
FIG. 11. Effect of incubation temperature and temperature treatment period on microspore embryogenesis of Caraway (var. NN-1) grown on AT-3 media. Each bar graph group represents data. The data representing a first harvest, followed seven days later by a second harvest, followed seven days later by a third harvest.
Figure 12:
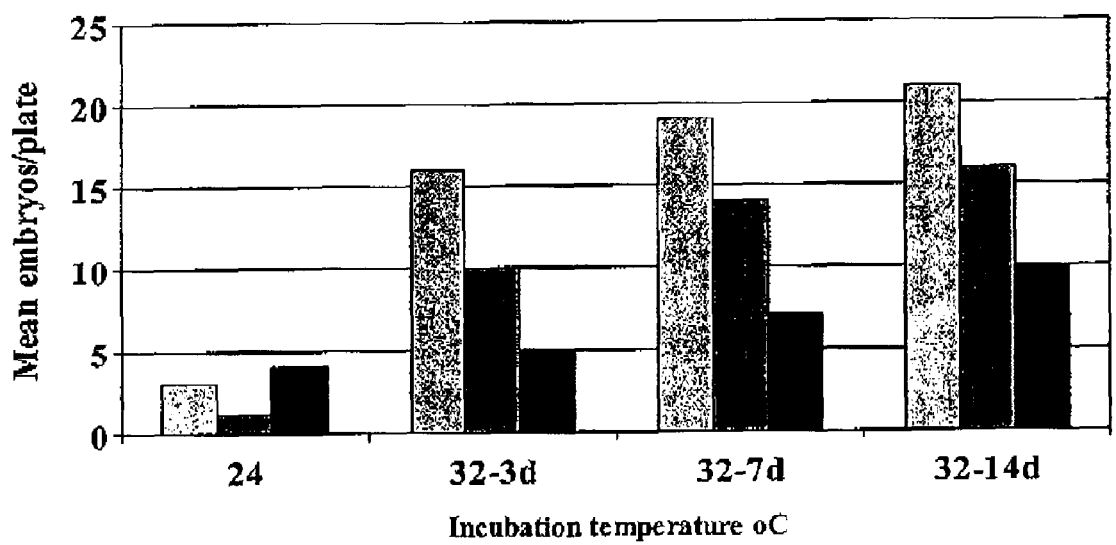
FIG. 12. Effect of incubation temperature and temperature treatment period on microspore embryogenesis of Caraway (var. NN-2) grown on AT-3 media. Each bar graph group represents data. The data representing a first harvest, followed seven days later by a second harvest, followed seven days later by a third harvest.

In order to optimize the culture medium for caraway, a number of different basal medium compositions were evaluated that included: B5 (Gamborg, 1968), NLN (Lichter, 1982), N6 (Chu, 1978), NN (Nitsch, et al., 1969), KM (Kao, et al., 1975), and AT-3 (Touraev et al. 1996). Embryos were produced on AT-3 basal media only (FIG. 9).

Another factor affecting embryogenesis is the age of the plants at which the microspores were harvested. Results indicate early harvests are better. Flowers collected from caraway plants 10 to 12 weeks from the date of planting produced more embryos than flowers collected from plants 12 weeks or older from date of planting. In an alternate embodiment, flowers are collected in 10 or fewer weeks from planting. In an alternate embodiment, flowers are collected in 11 or fewer weeks from planting. In an alternate embodiment, flowers are collected in 12 or fewer weeks from planting.

Regeneration & Plantlet Development.

Embryos typically develop from cultured, isolated microspores within three to ten weeks. However, some embryos were observed to form as late as 34 weeks after initial culture. Genotype VF2 for fennel was the most responsive and produced the greatest number of embryos under all conditions tested. Embryos from the genotypes appeared morphologically normal and similar. The majority of the embryos germinated and developed into plantlets. Likewise, for caraway, embryos typically develop from cultured, isolated microspores within three to ten weeks. Secondary embryogenesis was also observed on the caraway embryos.

Once embryos advanced to the cotyledonary stage of development, cultures were placed on a gyratory shaker in light for 1-2 weeks. Embryos were transferred to solidified B5 medium (1% sucrose, 1% agar) to develop into plantlets. Once the plantlets were established, they were subcultured onto fresh solid media (2% sucrose, 0.8% agar) in large Petri plates (150 mm×25 mm) or Magenta boxes. The development of secondary embryos and the production of multiple shoots may occur in this species.

Individual haploid plantlets were treated with colchicine. Once the root system was well developed, roots of the plantlets were immersed in a solution comprising 0.34% colchicine for 1.5 hours, rinsed in water and placed in moistened peat-pellets (Jiffy-7). The pellets were placed in covered trays and kept in a growth cabinet at 20/15° C. After a few weeks, surviving plantlets were hardened off and transplanted to soil in pots. The pots were placed in a 20/15° C. growth cabinet until plantlets were well established. Thereafter, they were transferred to a 10/5° C. growth cabinet or directly into the greenhouse.

Isolated Microspore Culture of Additional Apiaceae Species.

The process described herein for the identification of culture requirements for generating microspore-derived embryos of fennel or caraway was applied to carrot, parsnip, anise, and dill. Microspore-derived embryos and doubled-haploid plantlets were generated for each of the above species.

The results achieved for carrot showed that carrot embryos may be generated under a range of medium compositions and inductive treatments. Carrot seeds were planted in 8 inch pots filled with REDI-EARTH™ (available from Sun-Gro Horticulture, Bellevue, Wash.) soil-less mix containing approximately 1 g of slow release fertilizer (14-14-14-Nutricote). The soil mixture was thoroughly soaked with water and two seeds were placed in each pot. Pots were placed in a lighted growth cabinet (20/15° C., 16 h photoperiod, 400 µmol $m^{-2}s^{-1}$) and watered three times per week with 0.35 g/L of 15-15-18 (N-P-K) fertilizer. After approximately six weeks, plants were vernalized in a growth cabinet with a day/night temperature regime of 10/5° C. Approximately 8 weeks later, the plants were moved to the greenhouse for floral development.

Carrot embryos were recovered with media containing the growth regulators ABA, IPA, or ACC at sucrose concentrations of 10, 13, 15, 17, 20, and 25%. Inductive culture temperatures ranged from continuous 24 or 32° C. treatments or higher temperature initial treatments of 35 or 37° C. for three days. Embryos were also observed to form in media with a pH of 5.2, 5.8, or 6.5. The results for carrot indicate that this species is flexible in terms of induction and medium requirements for formation of microspore-derived doubled haploid embryos. The greatest success for embryo induction was obtained using NLN-25% sucrose medium with an incubation period of 32° C. for 7 d.

Further experimentation with additional species demonstrated that microspore-derived embryos may be generated using the same strategy.

In various embodiments, conditions for microspore embryo formation in parsnip were NLN medium with 25% sucrose with the isolated microspores cultured at 32° C. for 7 d. Parsnip plants were grown and vernalized under conditions equivalent to carrot plants described herein.

In various embodiments, conditions for induction of embryos from isolated microspores of anise were NLN medium with 25% sucrose with the isolated microspores cultured at 32° C. for 3 days or 24° C. No vernalization was required for anise.

In various embodiments, conditions for induction of microspore-derived embryos of dill were NLN medium containing 25, 17, or 13% sucrose wherein the isolated microspores were cultured at 32° C. for 3, 7, or 14 days. Donor plants were grown at 20/15° C. No vernalization was required for dill.

The invention will be described in more detail with reference to the following examples. The examples serve only to illustrate the invention.

EXAMPLES

Example 1

Determination of Fennel Donor Plant Growth Temperature Requirements.

Donor plants for isolated microspore culture were prepared as follows. Seeds were placed on a wetted filter paper in a Petri plate, wrapped with parafilm and placed in the dark (24° C.) for 3-5 days to germinate. Six-inch pots were filled with REDI-EARTH™ soil-less mix containing approximately 1 g of slow release fertilizer (14-14-14-Nutricote). The mixture was thoroughly soaked with water and one germinated seed was placed in each pot. Pots were placed in a lighted growth cabinet (20/15° C., 16 h photoperiod, 400 µmol $m^{-2}s^{-1}$) and watered three times weekly with 0.35 g/L of 15-15-18 (N-P-K) fertilizer. After approximately six weeks, growth cabinet temperatures were adjusted to a day/night temperature regime of 10/5° C. Approximately six weeks later, a selection of donor plants that are to be maintained at the 15/10° C. or 17/13° C. temperatures were moved to other growth cabinets set for these conditions.

Results shown in FIG. 1 represent the combined values of all genotypes tested. Embryos were recovered from donor plants grown under all conditions evaluated. However, the highest frequency of embryogenesis was from donor plants grown at 15/10° C. In all figures and tables, "embryos" refers to the number of good quality embryos that would be expected to germinate directly into morphologically normal plantlets. These embryos were transferred to solid medium for further analysis and plantlet production.

Example 2a

Determination of the Optimal Basal Medium Composition for Culture of Fennel Microspores.

Several basal media were compared for fennel microspore embryogenesis. Donor plants for microspore culture were grown as described herein. Flower buds were measured and buds in the range of 1-3 mm were put into Lipshaw baskets. The Lipshaw baskets were immersed for one minute in 70% ethanol in a sterile beaker and placed on a shaker. After one minute, the ethanol was removed and the baskets containing the buds were rinsed with sterile water. The Lipshaw baskets were immersed for 15 min in 6% sodium hypochlorite in a sterile beaker placed on a shaker. After 15 min, the sodium hypochlorite was removed by three 5-min washes with sterile water. The buds were removed from the Lipshaw baskets with sterile forceps and placed in a mortar with 5 mL of half-strength Gamborg B5 medium with 13% sucrose. The buds were gently crushed with a pestle, and the resulting suspension was filtered through a 44 µm nylon screen cloth into a 50 mL sterile centrifuge tube. The mortar and filter were rinsed three times with 5 mL of half-strength B5-13 which was filtered and added to the suspension to a total of 20 mL. The suspension was centrifuged at 130-150×g for 3 min. The resulting supernatant was removed and 5 mL of half-strength B5-13 was added to the pellet for resuspension. This procedure was repeated two additional times. Isolated microspores were placed into media with differing basal composition and cultured at 32° C. for 3 days. The best results were achieved with NLN medium.

Example 2b

Determination of the Optimal Basal Medium Composition for Culture of Caraway Microspores.

Donor plants for microspore culture were grown as described herein. Plants were thinned to one or two plants per pot. Flower buds were selected and put into Lipshaw baskets. The Lipshaw baskets were immersed for one minute in 70% ethanol in a sterile beaker and placed on a shaker. After one minute, the ethanol was removed and the baskets containing the buds were rinsed with sterile water. The Lipshaw baskets were then immersed for 15 min in 6% sodium hypochlorite in a sterile beaker placed on a shaker. After 15 min, the sodium hypochlorite was removed by three 5-min washes with sterile water. The buds were removed from the Lipshaw baskets with sterile forceps and placed in a mortar with 10 ml of wash medium. The buds were gently crushed with a pestle, and the resulting suspension was filtered through a 90 μm nylon screen cloth into a 50 mL sterile centrifuge tube. The mortar and pestle were rinsed three times with 10 mL of wash medium, which was filtered and added to the suspension to a total of 40 ml. The 90 um screen and funnel were then transferred to a fresh tube and rinsed with a further 40 ml of wash medium. Each suspension was then passed through a 44 μm screen for further purification. The suspension was then centrifuged at 130-150-×g for 3 min. The resulting supernatant was removed and 5 ml wash medium was added to the pellet for resuspension. This procedure was repeated two additional times. The contents of the tubes were combined and microspore density was determined using a haemocytometer. Isolated microspores were resuspended in AT-3 media.

Example 3

Determination of the Optimal Sucrose Concentration for Induction of Fennel Embryos.

Figure 3:
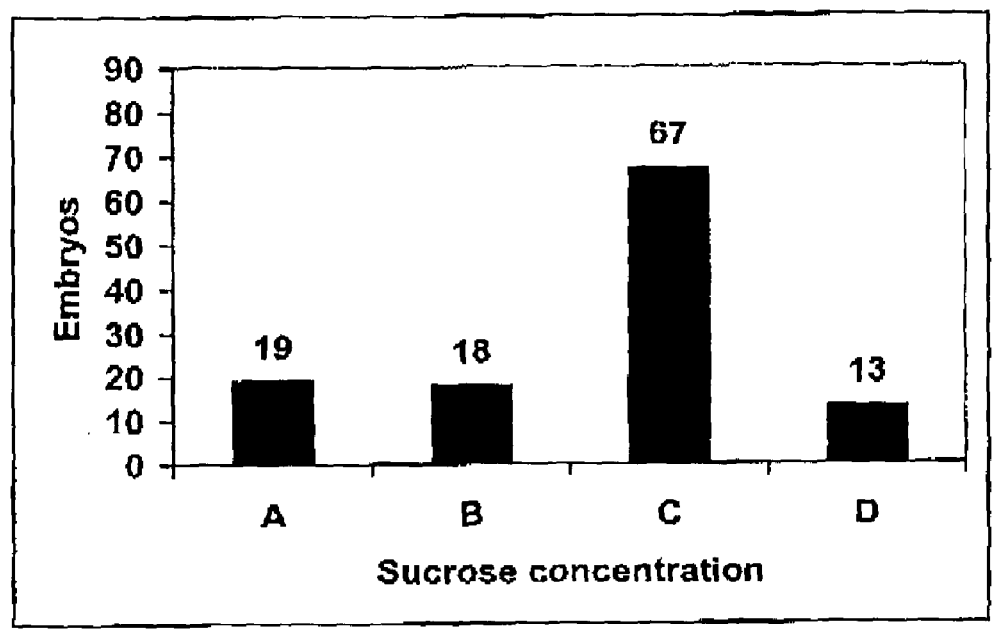
FIG. 3. Effect of sucrose concentration and media change on microspore embryogenesis of vegetable fennel (VF-10). A=NLN-25; B=NLN-25 changed to NLN-17 after 3 days; C=NLN-25 changed to NLN-13 after 3 days; and D=NLN13.
Figure 4:
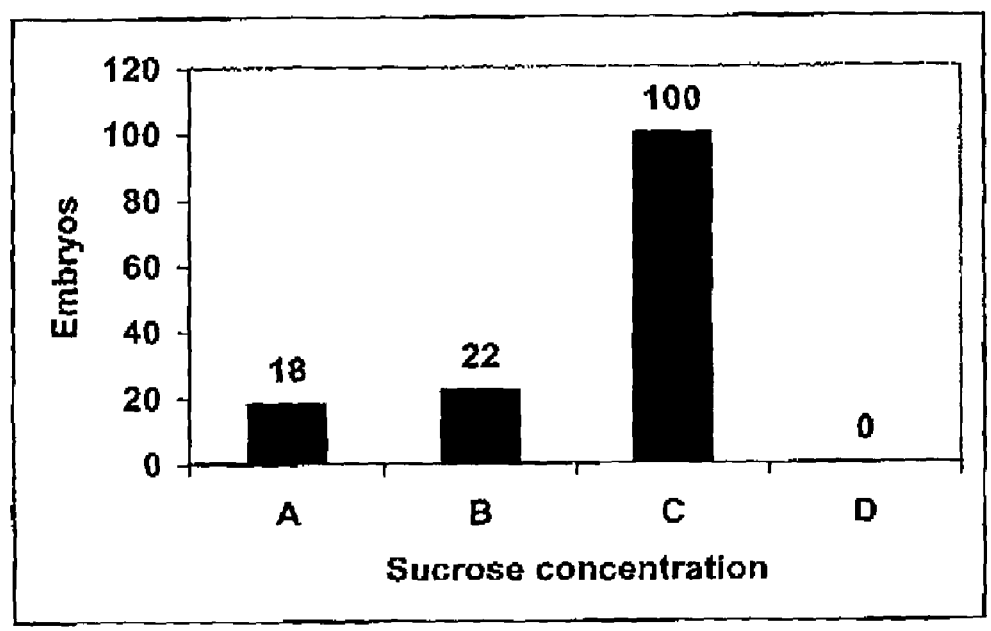
FIG. 4. Effect of sucrose concentration and media change on microspore embryogenesis of vegetable fennel (VF-4). A=NLN-25; B=NLN-25 changed to NLN-17 after 3 days; C=NLN-25 changed to NLN-13 after 3 days; and D=NLN13.

Microspores were subjected to embryo induction in media comprising sucrose at differing concentrations. The impact of culturing at high sugar concentrations for 3 d followed by switching to a medium with lower sucrose concentration was evaluated. All microspores were cultured in NLN with 25% sucrose. After 3 days, the medium was removed from each Petri dish and placed into a centrifuge tube. The tubes were centrifuged at 130-150×g for 3 minutes. The supernatant was removed and fresh medium was added. This fresh medium was NLN with 10, 13, 15, 17, or 25% sucrose. Initial culture in the medium with 25% sucrose was followed by a medium change to NLN with 13% sucrose was the preferred treatment. The positive impact of initial high temperature induction in media comprising 25% sucrose followed by the transfer of isolated microspores to media comprising 13% sucrose which is shown for two vegetable fennel lines in FIGS. 3 and 4, respectively.

Example 4a

Determination of the Optimal Medium Sugar Composition for Fennel Embryo Induction at Elevated Temperature.

Six different carbohydrates (fructose, glucose, maltose, melibiose, melezitose, and raffinose) were evaluated using NLN as the basal culture medium. Six different concentrations of these carbohydrates was evaluated; similar osmolarities to 10%, 13%, 15%, 17%, 20%, and 25% sucrose. Due to solubility limitations, raffinose was evaluated at two different concentrations (equivalent osmolarity to 8% and 16% sucrose). After 72 h of culture, the microspores in media containing 25% carbohydrate were transferred to media with lower concentrations of sugars as shown in FIG. 7, which shows the results for genotype VF-10. Three temperature regimes were also simultaneously evaluated (32, 35, and 37° C.). No embryos were formed in incubations at 37° C.

At an inductive temperature of 35° C., the best results for fennel were achieved with glucose (25%) as the medium carbohydrate, followed subsequently (in three days) with a transfer to a glucose medium with lower osmolarity (similar to that of 17% sucrose). However, at an induction temperature of 32° C., sucrose was the better carbohydrate source for embryo formation for fennel.

Example 4b

Determination of the Optimal Sugar Composition for Caraway Embryo Induction

Experiments evaluated the culture media, AT-3 with 9% maltose and AT-3 with sucrose. There was no development in the AT-3 medium containing sucrose. However, the microspores in the medium with maltose did develop embryos.

Example 5

Influence of 24 Epibrassinolide (EBR) on Isolated Microspore Embryo Fennel Formation.

EBR was dissolved in dimethyl sulfoxide (DMSO) to achieve stock solutions of 0.1, 1.0, and 10 mM and stored at room temperature. EBR was added at various concentrations to the culture medium with the DMSO concentration remaining constant at 0.1% v/v (Wilen et al. 1995). All experiments included untreated and 0.1% (v/v) DMSO-treated control cultures. EBR was added to the initial media used for culture (NLN-25) of the microspores. Microspores were cultured at 32° C. for 3 days. After 3 days, the medium was changed to NLN with a lower concentration of sucrose with or without EBR and cultures were maintained at 24° C.

Figure 5:
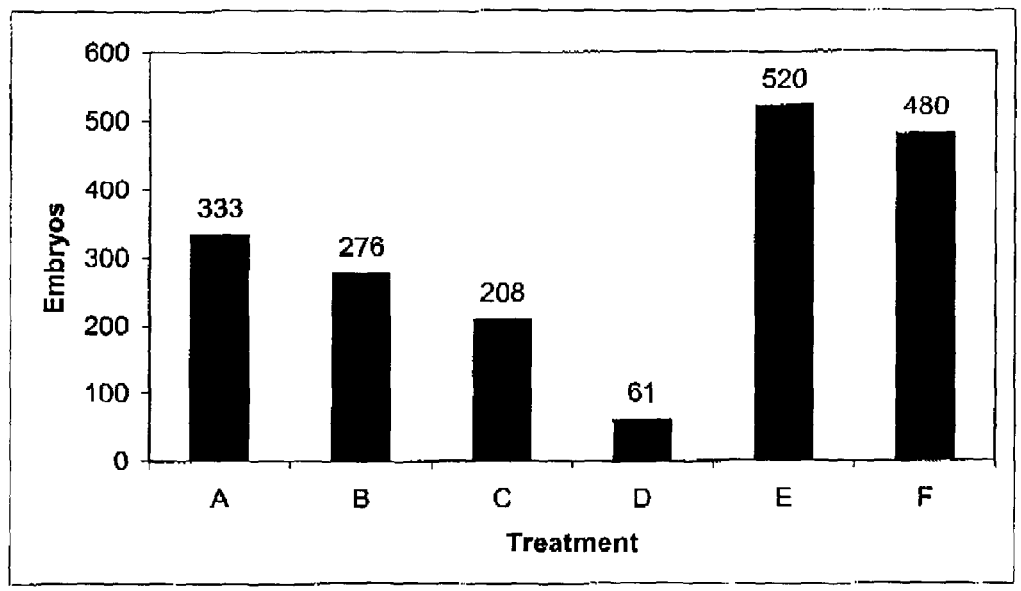
FIG. 5. Effect of 24-Epibrassinolide on microspore embryogenesis of vegetable fennel (VF-2). A=NLN-25; B=NLN-25+0.1 mM EBR; C=NLN-25+1.0 mM EBR; D=NLN-25 changed to NLN-10; E=NLN-25+0.1 mM EBR changed to NLN-10; and F=NLN-25+1.0 mM EBR changed to NLN-10.

Results shown in FIG. 5 demonstrate that the continued exposure to 24 EBR was somewhat inhibitory to fennel embryo formation. However, a media change after 72 h to a lower sucrose concentration and a removal of the 24-EBR was stimulatory to fennel embryo formation.

Example 6

Genotypic Differences in Response to EBR by Cultured Isolated Microspores of Vegetable Fennel.

Figure 6:
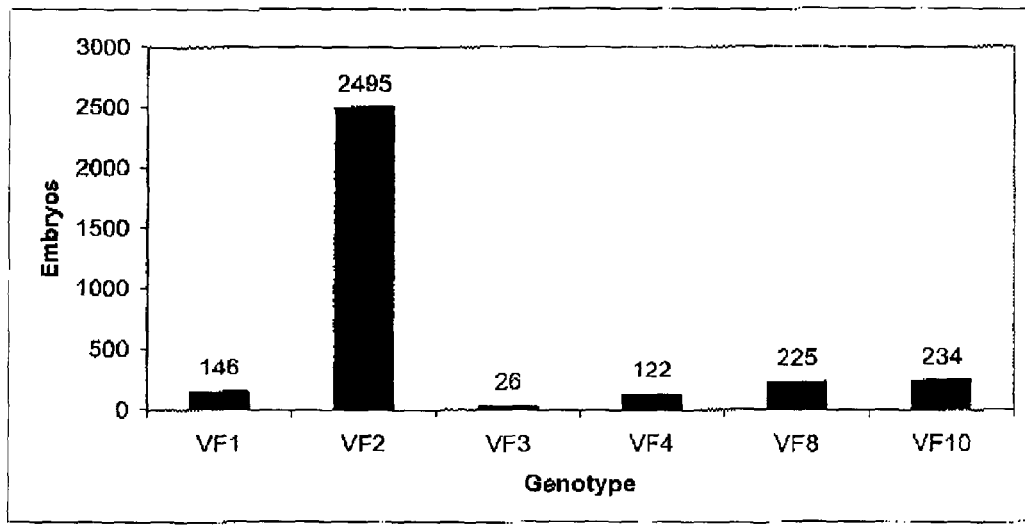
FIG. 6. Embryogenic response of different fennel genotypes.

Dramatic differences in the response of different vegetable fennel genotypes were demonstrated when EBR was included in the culture medium. Donor plants were prepared as described in Example 1 and cultured in media with 25% sucrose. Results shown in FIG. 6 demonstrate that line VF2 was much more responsive that the other lines.

Example 7

Determination of Optimal Temperature for Caraway Induction

Experiments in which caraway microspores were subjected to 24° C. continuous or 32° C. for 3, 7, or 14 days then 24° C., demonstrated that embryos could be recovered at all temperature regimes, however there was a higher frequency of embryogenesis from those microspores induced at 32° C.

then at 24° C. Results further indicated that the longer the 32° C. heat shock, the greater the frequency of embryogenesis.

Example 8

Growth of Caraway Plantlets

Once caraway embryos advanced to the cotyledonary stage of development, they were transferred to solidified B5 medium (1% sucrose, 1% agar) to develop into plantlets. Individual haploid plantlets were treated with colchicine to induce chromosome doubling. Once the root system was well developed, the plates were flooded with 10 ml of 0.34% colchicine in sterile glass-distilled water and returned to the tissue culture chamber (16 hr. photoperiod, 22 degrees constant) for at least 12 hours. Plantlets were then removed from the plates, rinsed in distilled water and planted in REDI-EARTH™ in 10 cm square nursery pots. The plantlets were covered with clear polystyrene cups to maintain high humidity. After a few weeks, surviving plantlets were hardened off and transplanted to soil-less mix in pots. The pots were placed in a 20/15° C. growth chamber. As plants matured and produced flowers, they were bagged to ensure self-fertilization. Seeds were allowed to develop and were harvested when mature.

Example 9

Embryo Formation from Isolated Microspores of Additional Apiaceae Species.

Embryos were obtained from a number of additional Apiaceae species including: angelica, anise, carrot, dill, laceflower, lovage, and parsnip, following the procedural strategy outlined in the specification and described in detail for fennel in the examples herein.

Donor plants of angelica, anise, laceflower, and dill were grown as described in Example 1. Donor plants of carrot, lovage, and parsnip were vernalized to induce flowering Seeds were planted in six-inch pots filled with REDI-EARTH™ soil-less mix containing approximately 1 g of slow release fertilizer (14-14-14-Nutricote). The mixture was soaked thoroughly with water and two to four seeds were placed in each pot. Pots were placed in a lighted growth cabinet (20/15° C., 16 hour photoperiod, 400 µmol m$^{-2}$s$^{-1}$) and watered three times per week with 0.35 g/L of 15-15-18 (N-P-K) fertilizer. After germination, plants were thinned to one or two per pot. After approximately six weeks, plants were vernalized using a growth cabinet set at 10/5° C. Approximately 8 weeks later, the plants were moved to the greenhouse. Microspores were isolated as described in Example 2b.

All references, including publications, patents, and patent applications, cited herein are hereby incorporated by reference to the same extent as if each reference were individually and specifically indicated to be incorporated by reference and were set forth in its entirety herein.

REFERENCES

The Contents of which are Hereby Incorporated by this Reference

1. Arnison, P. G., et al. Genotype specific response of cultured broccoli (*B. oleracea* var *italica*) anthers to cytokinins. Plant Cell, Tissue and Organ Culture 20:217-222. (1990)
2. Barro, F., et al. Response of different genotypes of *Brassica carinata* to microspore culture, Plant Breeding 118: 79-81. (1999)
3. Brossa C. Biological effects of brassinosteroids. Critical Reviews in Biochemistry and Molecular Biology 34:339-358. (1999)
4. Chu, C. C. The N6 medium and its applications to anther culture of cereal crops. Science Press 43-50. (1978)
5. Cordwener, J. H. G., et al. Induction of microspore embryogenesis in *Brassica napus* L. is accompanied by specific changes in protein synthesis. Planta. 195:50-56. (1994).
6. Dunwell, J. M. Pollen, ovule and embryo culture as tools in plant breeding. In: Plant Tissue Culture and its Agricultural Applications, L. A. Withers and P. G. Alderson (eds) Butterworth, London. (1986)
7. Fabijanski, S. F., et al. Heat shock response during anther culture of broccoli (*B. oleracea* var *italica*). Plant Cell, Tissue and Organ Culture 26:203-212. (1991)
8. Fan, Z., et al. Development of microspores in vivo and in vitro in *Brassica napus* L. Protoplasma. 147:191-199. (1988).
9. Ferrie, A. M. R., et al. Effects of brassinosteroids on microspore embryogenesis in *Brassica* species. In Vitro Cellular and Developmental Biology Plant 41: 742-745 (2005).
10. Ferrie, A. M. R., et al. Biotechnology applications for haploids. In: Biotechnological Applications of Plant Cultures. Shargool, P. D. and Ngo, T. T., (eds.), CRC Press, Boca Raton, p 77-110. (1994)
11. Ferrie, A. M. R., et al. Evaluation of *Brassica rapa* L. genotypes for microspore culture response and identification of a highly embryogenic line. Plant Cell Reports 14: 580-584. (1995)
12. Fete, A. M. R., et al. Haploid Embryogenesis. In: In Vitro Embryogenesis in Plants, pp 309-344. (1995)
13. Ferrie, A. M. R. et al. Microspore culture for haploid plant production. In: O. L. Gamborg, and G. G. Phillips (eds.) Plant Cell, Tissue and Organ Culture: fundamental methods. Springer. Berlin, pp. 155-164, (1995)
14. Ferrie, A. M. R., et al. *Brassica* improvement through microspore culture. Biotechnology in Agriculture and Forestry Vol. 54: *Brassica*. E. C. Pua and C. J. Douglas. Berlin, Springer-Verlag: 149-168. (2004)
15. Ferrie, A. M. R., et al. Microspore embryogenesis of high sn-2 erucic acid *Brassica oleracea* germplasm. Plant Cell, Tissue and Organ Culture 57: 79-84. (1999)
16. Gaillard, A., et al. Optimization of maize microspore isolation and culture conditions for reliable plant regeneration. Plant Cell Reports 10:55-58. (1991)
17. Gamborg, O. L., et al. Nutrient requirements of suspension cultures of soybean root cells. Exp. Cell Res. 50:151-158. (1968)
18. Grove, M. D., et al. Brassinolide, a plant growth promoting steroid isolated from *Brassica napus* pollen. Nature 281:216-217. (1979)
19. Kao, K. N., et al. Nutritional requirements for growth of *Vicia hajastana* cells and protoplasts at a very low population density in liquid media. Planta 126:105-110. (1975)
20. Keller W. A., et al. High frequency production of microspore-derived plants from *Brassica napus* anther cultures. Z. Pflanzenzuchtg. 80:100-108. (1978)
21. Kott, L. S., et al. Cytological aspects of isolated microspore culture of *Brassica napus*. Can. J. Bot. 66:1658-1664. (1988)
22. Krishna, P. Brassinosteroid-mediated stress responses. J. Plant Growth Reg. 22:289-297. (2003)
23. Lichter, R. Induction of haploid plants from isolated pollen of *Brassica napus*. Z. Pflanzenphysiol 105:427-434. (1982)

24. Lionneton, E., et al. Improved microspore culture and doubled-haploid plant regeneration in the brown condiment mustard (*Brassica juncea*). Plant Cell Reports 20:126-130. (2001)
25. Lu Z., et al. Effect of brassinolide on callus growth and regeneration in *Spartina patens* (Poaceae). Plant Cell, tissue and Organ Culture 73:87-89 (2003)
26. Maheshwari, S. C., et al. Haploids from pollen grains—retrospect and prospect. Amer. J. Bot. 69: 865-879. (1982)
27. Nakajima, N., et al. Effects of brassinosteroid on cell division and colony formation of Chinese cabbage mesophyll protoplasts. Japanese Journal of Crop Science 65:114-118. (1996)
28. Oh, M. H., et al. Brassinolide affects the rate of cell division in isolated leaf protoplasts of *Petunia hybrida*. Plant Cell Reports 17:921-924. (1998)
29. Polsoni, L., et al. Large-scale microspore culture technique for mutation-selection studies in *Brassica napus*, Canadian Journal of Botany 66:1681-1685. (1988)
30. Pullman, G. S., et al. Brassinolide improves embryogenic tissue initiation in conifers and rice. Plant Cell Reports 22:96-104 (2003)
31. Nitsch, J. P., et al., Haploid plants from pollen grains. Science 163:85-87. (1969)
32. Saskaki, R. Brassinolide promotes adventitious shoot regeneration from cauliflower hypocotyl segments. Plant Cell, tissue and Organ Culture 71:111-116. (2002)
33. Sasse, J. M. Physiological actions of brassinosteroids. Brassinosteroids: Steroidal Plant Hormones. A. Sakurai, T. Yokota and S. D. Clouse. Tokyo, Springer-Verlag: 137-161. (1999)
34. Wilen, R., et al. Effects of 24-epibrassinolide on freezing and thermotolerance of bromegrass (*Bromus inermis*) cell cultures. Physiologia Plantarum 95:195-202. (1995)
35. Zhao J P and Simmonds D H and Newcomb W. High frequency production of doubled-haploid plants of *Brassica napus* cv. Topas derived from colchicine-induced microspore embryogenesis without heat shock. Plant Cell Rep. 15: 668-671 (1996)

What is claimed is:

1. A method for producing a microspore-derived doubled haploid plant of the family Apiaceae, the method comprising:
   isolating microspores from flower buds of microspore donor plants, wherein the microspores are at a developmental stage competent for induction of embryo development;
   culturing the isolated microspores in a medium comprising NLN or AT-3;
   inducing embryogenesis in the isolated microspore cultures;
   recovering the microspore-derived embryos; and
   generating doubled haploid plants.

2. The method according to claim 1, wherein the medium comprises at least 10% total sugar and the sugar is selected from the group consisting of sucrose, glucose, maltose and combinations thereof.

3. The method according to claim 1, further comprising growing the microspore donor plants under a day/night temperature regime of 15/10° C., respectively.

4. The method according to claim 3, wherein the medium comprises at least 25% sucrose.

5. The method according to claim 3, wherein the medium comprises epibrassinolide (EBR).

6. The method according to claim 3, wherein isolating microspores from flower buds of microspore donor plant comprises selecting a VF1, VF2, VF3, VF4, VF8 or VF10 genotype of fennel microspore donor plant.

7. The method according to claim 3, wherein isolating microspores from flower buds of microspore donor plant comprises selecting a VF2 genotype of fennel microspore donor plant.

8. The method according to claim 1, further comprising growing microspore donor plants under a day/night temperature regime of 20/15° C., respectively.

9. The method according to claim 8, wherein isolating microspores from flower buds of microspore donor plants further comprises isolating microspores from flower buds of microspore donor plants less than twelve weeks after the microspore donor plants are planted.

10. The method according to claim 9, wherein isolating microspores from flower buds of microspore donor plants further comprises isolating microspores from flower buds of microspore donor plants ten to twelve weeks after the microspore donor plants are planted.

11. The method according to claim 8, wherein the medium comprises at least 9% maltose.

12. The method according to claim 1, wherein inducing embryogenesis comprises culturing the isolated microspores at a temperature in a range of 30-35° C. for up to fourteen days.

13. The method according to claim 12, wherein inducing embryogenesis further comprises subsequently changing the temperature to 24° C.

14. The method according to claim 1, wherein isolating microspores from flower buds of microspore donor plants comprises isolating microspores from 1-3 mm flower buds of fennel or caraway microspore donor plants.

15. The method according to claim 1, wherein culturing isolated microspores in a medium comprises culturing about 50,000 microspores per mL.

16. A method for producing a microspore-derived embryo of a member of the Apiaceae (Umbelliferae) family of plants, the method comprising:
   isolating microspores from flower buds of microspore donor plants;
   culturing the isolated microspores in a medium comprising NLN or AT-3;
   inducing embryogenesis in the isolated microspore cultures; and
   generating a microspore-derived embryo.

* * * * *